US011242519B2

(12) United States Patent
Stelling

(10) Patent No.: US 11,242,519 B2
(45) Date of Patent: *Feb. 8, 2022

(54) DISCONTINUOUS WALL HOLLOW CORE MAGNET

(71) Applicant: Alpaqua Engineering, LLC, Beverly, MA (US)

(72) Inventor: Olaf Stelling, Beverly Farms, MA (US)

(73) Assignee: Alpaqua Engineering, LLC, Beverly, MA (US)

( * ) Notice: Subject to any disclaimer, the term of this patent is extended or adjusted under 35 U.S.C. 154(b) by 827 days.

This patent is subject to a terminal disclaimer.

(21) Appl. No.: 16/110,543

(22) Filed: Aug. 23, 2018

(65) Prior Publication Data
US 2020/0063118 A1 Feb. 27, 2020

(51) Int. Cl.
| | |
|---|---|
| *B01L 9/06* | (2006.01) |
| *G01N 33/543* | (2006.01) |
| *C12N 15/10* | (2006.01) |
| *B03C 1/01* | (2006.01) |
| *B03C 1/28* | (2006.01) |
| *G01N 35/00* | (2006.01) |
| *B03C 1/033* | (2006.01) |

(52) U.S. Cl.
CPC ............ *C12N 15/1013* (2013.01); *B03C 1/01* (2013.01); *B03C 1/0332* (2013.01); *B03C 1/288* (2013.01); *G01N 33/54326* (2013.01); *G01N 35/0098* (2013.01); *B03C 2201/18* (2013.01); *B03C 2201/22* (2013.01)

(58) Field of Classification Search
CPC ..... C12N 15/1013; B03C 1/01; B03C 1/0332; B03C 2201/18; B03C 2201/22; B03C 1/288; B03C 1/286; G01N 33/54326; G01N 35/0098; B01L 9/06; B01L 2300/0609
USPC ........................................................ 536/25.6
See application file for complete search history.

(56) References Cited

U.S. PATENT DOCUMENTS

| | | | |
|---|---|---|---|
| 4,162,674 | A | 7/1979 | Klein |
| 5,186,827 | A | 2/1993 | Liberti et al. |
| 5,519,373 | A | 5/1996 | Miyata |
| 5,571,481 | A | 11/1996 | Powell et al. |

(Continued)

FOREIGN PATENT DOCUMENTS

| | | |
|---|---|---|
| DE | 20 2014 102 945 U1 | 8/2014 |
| EP | 0 589 636 A1 | 3/1994 |

(Continued)

OTHER PUBLICATIONS

International Preliminary report on Patentability for PCT/US2015/0556112, dated Apr. 27, 2017.

(Continued)

*Primary Examiner* — Charles A Fox
*Assistant Examiner* — Molly K Devine
(74) *Attorney, Agent, or Firm* — Antoinette G Giugliano; Antoinette G Giugliano PC

(57) ABSTRACT

A discontinuous wall magnet having an opening or channel is provided. A bead separation magnet having a discontinuous or segmented wall is also provided. The segmented wall causes bead formation to form in a segmented or gapped ring to allow for easier manual pipetting. Also provided are systems and kits having the inventive magnets. Methods of purifying a macromolecule using the inventive magnets are also provided.

26 Claims, 6 Drawing Sheets

(56) References Cited

U.S. PATENT DOCUMENTS

| | | |
|---|---|---|
| 5,705,062 A | 1/1998 | Knobel |
| 5,733,405 A | 3/1998 | Taki |
| 5,733,442 A | 3/1998 | Shukla |
| 6,255,478 B1 | 7/2001 | Komai et al. |
| 6,755,384 B2 | 6/2004 | Gorfain |
| 6,764,859 B1 | 7/2004 | Kreuwel et al. |
| 6,870,047 B2 | 3/2005 | Kleiber et al. |
| 7,384,559 B2 | 6/2008 | a Brassard |
| 7,474,184 B1 | 1/2009 | Humphries et al. |
| 7,551,051 B2 | 6/2009 | Ugai et al. |
| 7,718,072 B2 | 5/2010 | Safar et al. |
| 8,062,846 B2 | 11/2011 | Bortolin et al. |
| 8,071,395 B2 | 12/2011 | Davis et al. |
| 8,597,878 B2 | 12/2013 | Hillebrand et al. |
| 8,658,042 B2 | 2/2014 | Fasching |
| 8,703,931 B2 | 4/2014 | Euting et al. |
| 9,140,634 B1 | 9/2015 | Knippschild et al. |
| 9,416,399 B2 | 8/2016 | Euting et al. |
| 9,663,780 B2 | 5/2017 | Stelling |
| 10,087,438 B2 | 10/2018 | Stelling |
| 10,208,303 B2 | 2/2019 | Stelling |
| 2001/0014466 A1 | 8/2001 | Lubenow et al. |
| 2004/0142384 A1 | 7/2004 | Cohen et al. |
| 2005/0072674 A1 | 4/2005 | Heins et al. |
| 2006/0055266 A1 | 3/2006 | Iwami et al. |
| 2006/0158292 A1 | 7/2006 | Ugai et al. |
| 2007/0182517 A1 | 8/2007 | Humphries et al. |
| 2007/0218566 A1 | 9/2007 | Barten et al. |
| 2008/0171337 A1 | 7/2008 | Miyazaki et al. |
| 2008/0199365 A1 | 8/2008 | Chu |
| 2008/0206751 A1 | 8/2008 | Squirrell et al. |
| 2010/0227387 A1 | 9/2010 | Safar et al. |
| 2010/0311608 A1 | 12/2010 | Osada et al. |
| 2014/0186236 A1 | 7/2014 | Euting et al. |
| 2016/0108392 A1 | 4/2016 | Stelling |
| 2016/0368001 A1* | 12/2016 | Park .................... B03C 1/0332 |
| 2017/0226502 A1 | 8/2017 | Stelling |
| 2018/0028990 A1 | 2/2018 | Frodsham et al. |
| 2018/0362963 A1 | 12/2018 | Stelling |
| 2018/0362964 A1 | 12/2018 | Stelling |
| 2019/0160473 A1 | 5/2019 | Stelling |
| 2020/0063118 A1 | 2/2020 | Stelling |
| 2020/0181684 A1 | 6/2020 | Tiedtke et al. |

FOREIGN PATENT DOCUMENTS

| | | | | |
|---|---|---|---|---|
| EP | 1404450 B1 | 11/2005 | | |
| EP | 2082806 A2 | 7/2009 | | |
| EP | 2 565 260 A2 | 3/2013 | | |
| WO | WO 1996/15440 | 5/1996 | | |
| WO | WO 2000/23807 | 4/2000 | | |
| WO | WO 2003/044537 A1 | 5/2003 | | |
| WO | WO-03090897 A1 * | 11/2003 | ............ | B01D 35/06 |
| WO | WO 2005/008209 A2 | 1/2005 | | |
| WO | WO 2005/008861 A1 | 1/2005 | | |
| WO | WO 2006/072593 A2 | 7/2006 | | |
| WO | WO-2009076560 A2 * | 6/2009 | ............... | B03C 1/01 |
| WO | WO 2014/007074 A1 | 1/2014 | | |
| WO | WO2016061285 | 4/2016 | | |
| WO | WO2019057345 A1 | 3/2019 | | |
| WO | WO2020041339 | 2/2020 | | |
| WO | WO2020041345 | 2/2020 | | |

OTHER PUBLICATIONS

International Search Report and Written Opinion, PCT application No. PCT/US2019/047310, dated Oct. 9, 2019.
Brochure "Alpaqua Liquid Handling Products, MagPlate 24, 24-well Magnet Plate", Alpaqua Engineering, LLC, 100 Cummings Center, Suite 424A Beverly, MA 01915 (2011).
Brochure "Alpaqua Accelerating Genomic Discovery, MagPlate 24, 24-well Magnet Plate", Alpaqua Engineering, LLC, 100 Cummings Center, Suite 424A Beverly, MA 01915 (2011).
International Search Report and Written Opinion, PCT application No. PCT/US2019/047302, dated Nov. 22, 2019.
Communication pursuant to Article 94(3) EPC for EP Application No. 15790728.8, dated May 15, 2018, Alpaqua Engineering, LLC.
International Preliminary report on Patentability, dated Apr. 27, 2017, Alpaqua Engineering, LLC.
Schimp, Paul H "A Detailed Explanation of Solenoid Force" *Int. J. on Recent Trends in Engineering and Technology*, 8(2):7-14 (Jan. 2013).
PCT International Search Report for PCT PCT/US2015/0556112, dated Jan. 14, 2016, Alpaqua Engineering, LLC.
Written Opinion of the International Searching Authority for PCT PCT/US2015/0556112, dated Jan. 14, 2016, Alpaqua Engineering, LLC.
International Preliminary Report on Patentability, PCT application No. PCT/US2019/047302, dated Mar. 4, 2021.
International Preliminary Report on Patentability, PCT application No. PCT/US2019/047310, dated Mar. 4, 2021.

* cited by examiner

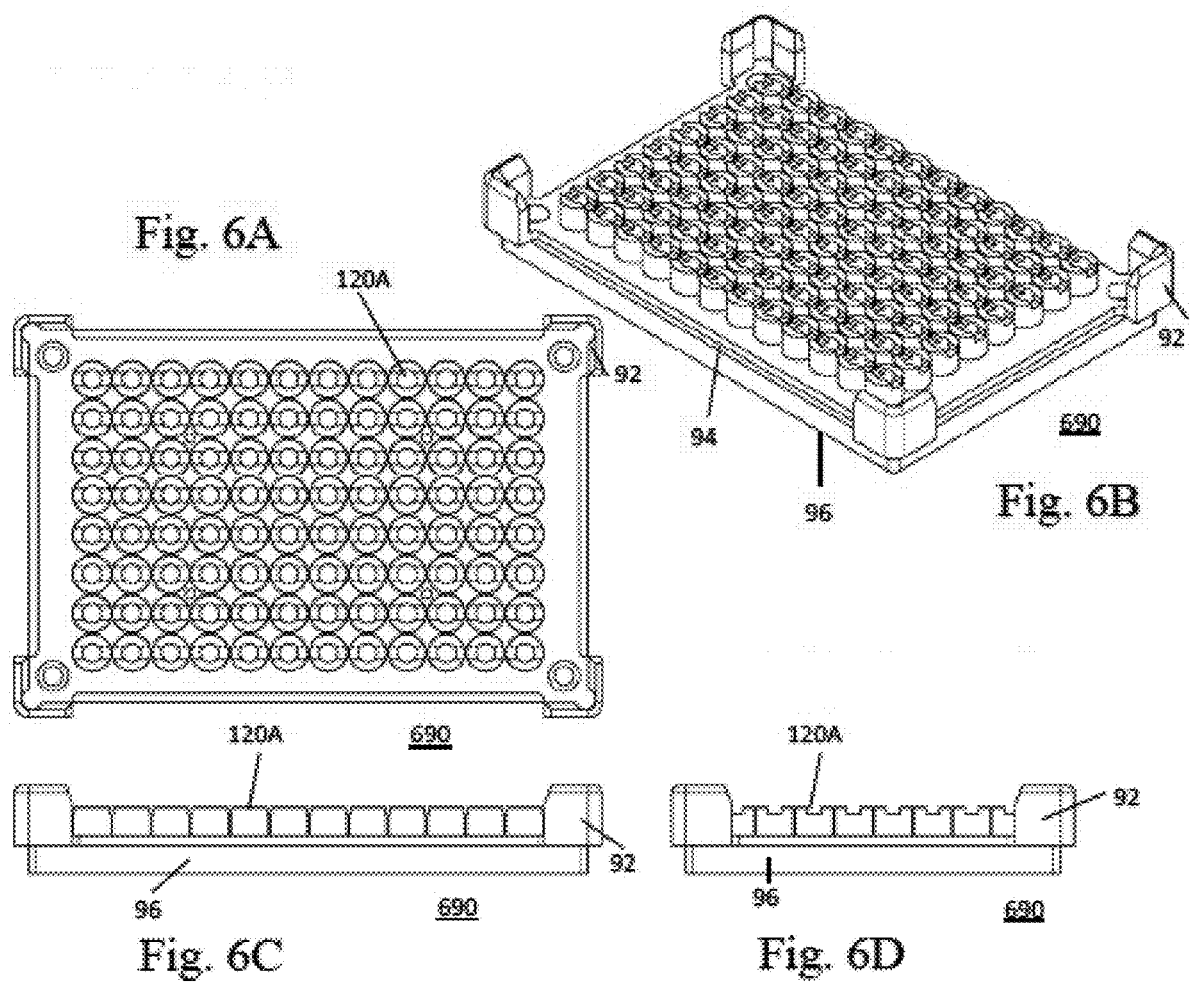

DISCONTINUOUS WALL HOLLOW CORE MAGNET

BACKGROUND OF THE INVENTION

Many analytical methods in the field of molecular biological research often require the isolation of macromolecules for further study. For example, the burgeoning field of genomic research compels efficient isolation and purification of nucleic acids—most commonly DNA and RNA—from a variety of biological samples, such as plasmids, tissue samples, blood or other bodily fluids, archived samples (FFPE samples), and many others. Nucleic acids can be purified via a variety of methods, including the traditional phenol-chloroform extraction, ethanol extraction, or spin columns. One disadvantage of these methods is their reliance on centrifugation and/or vacuum steps, which have traditionally been hard to automate. Advances in sequencing technology in recent decades presented a need for automatable methods capable of extracting nucleic acids at high throughput rates. To that end, the use of magnetic beads has emerged as the method of choice because it is simple, inexpensive, efficient, and can be performed manually or by automated pipettors.

In this technology, microscopic paramagnetic beads are coated with application-specific functional groups that allow reversible binding of either nucleic acids, proteins, or other macromolecules. To achieve the reversible bond, the biological sample is mixed with a solution of the magnetic beads under chemical conditions that support the affinity of the macromolecules to the magnetic bead. This mixture is subsequently exposed to a magnetic field, leading to sequestration and immobilization of the magnetic beads together with the macromolecule of interest. Following this step, the supernatant, which is that portion of the sample fluid that remains after the macromolecule of interest has been extracted, is removed and discarded. While still immobilized by the magnetic field, the bead-macromolecule complex is washed to further remove contaminants. Finally, a buffer is added to the bead complex, which changes the chemical conditions (pH, salt concentration) necessary to maintain the bond between macromolecules and beads. This change in conditions initiates the elution process, whereby the macromolecules are released from the magnetic beads (still immobilized) and are now free-floating in the elution buffer in purified form.

The magnetic field used to immobilize the magnetic beads is commonly provided by magnets. One example of a magnet used in bead separation techniques is a standard ring magnet. When standard ring magnets are positioned below the reaction vessel, the magnetic beads aggregate where the magnetic field is strongest and generally form a ring around the perimeter of the vessel bottom, reflecting the shape of the magnet. This leaves an area in the center of the ring that is mostly free of beads. Accordingly, in order to aspirate the supernatant, a pipet tip must be inserted into this area at the center of the vessel. When this action is performed, many times the technician inadvertently or accidentally aspirates beads along with the supernatant. This task can be very challenging for some when done manually. The smaller the bead ring, the more difficult to aspirate the supernatant without also accidentally aspirating the beads. Accordingly, a need exists for a system that allows for easier aspiration of the solution without inadvertent aspiration of the beads in the vessel when pipetting is performed manually.

SUMMARY OF THE INVENTION

Macromolecules, such as nucleic acids, can be separated or extracted via a variety of methods. In one method, complexes are formed between macromolecules and magnetic beads, and the magnetic beads are separated from a mixture, essentially purifying the macromolecules after their "un-complexation" or elution from the beads through changes in conditions. In an embodiment, the complex between the macromolecules and magnetic beads remains in the vessel aggregating to form of a pattern (e.g., a ring pattern, discontinued ring pattern, or other shaped pattern) and most of the solution is removed, leaving a high concentration of complex in the vessel.

In an embodiment, the present invention includes a magnet that can be used to isolate/purify macromolecules from a mixture. The mixture, as defined herein, is any aqueous solution that has at least the macromolecule in addition to the solvent. As an example, it can be extracellular matrix, cell debris, plasma, saliva, etc. The macromolecules, as defined here, encompass nucleic acids such as DNA or RNA, or proteins such as antibodies. The magnet, in particular, can be used to isolate macromolecules by making them adhere to magnetic beads, after which they can be separated from the mixture. In particular, through changes in the chemical environment macromolecules are made to adhere to the magnetic beads to form a complex. The magnet is then used to attract the complexes and pull them out of solution. In particular, the magnet of the present invention causes the complex to form an aggregation of bead complexes in a pattern within the vessel. The solution can then be removed leaving behind the magnetic beads with the macromolecules adhered thereto.

In an embodiment, the magnet encompassed by the present invention, in one aspect, has a top surface (a first surface) at one end, a bottom surface (e.g., a second surface) at another end, and an opening (e.g., tunnel, channel canal, or trough) that extends along the length of the magnet. More specifically, the magnet of the present invention has a wall (e.g., cylindrical wall) defining the opening extending from a first end having a first surface to a second end having a second surface. The magnet has one or more discontinuous walls (e.g., one at either or both ends) wherein at least a portion of the discontinuous wall comprises one or more segments and one or more gaps. The discontinuous wall forms a shape configured to form a magnetic field, when in use, within the vessel. The magnet has a side wall, for example, that surrounds the magnet. In an aspect, the wall creates a magnetic field that forms a discontinuous pattern in the vessel such that, when in use, the complex of macromolecules and paramagnetic beads aggregate and can be separated from the mixture. The discontinuous wall, in an embodiment, has one, two, three or four segments separated by one, two, three or four gaps, respectively, to form a discontinuous shape. The shape of the wall can form a discontinuous ring, oval, square, rectangular, triangular, diamond, or an irregular shape. The magnet of the present invention can be made from one or more pieces.

In another embodiment, a system for isolating macromolecules is disclosed. In addition to the magnet of the present invention, the system can include a vessel for holding a mixture that includes a macromolecule (e.g., DNA). The same types of magnets as encompassed by other embodiments can be included as part of the system as well.

Also disclosed are methods of purifying macromolecules from a liquid sample that contains a mixture. The methods, in an embodiment, include steps of collecting the liquid in a vessel, adding magnetic beads to the sample, and separating the magnetic bead-macromolecule complex from the sample by placing the vessel in the opening/channel of a magnet. After these steps, the macromolecule can be eluted from the magnetic beads. In an embodiment, the sample can include an extracellular matrix and the method may further include a step of lysing the sample before adding magnetic beads to the sample. The method further includes a step of pipetting sample manually or using an automated pipette. When pipetting manually, one can do so at one or more gaps in the wall, which allows one to access the gap in the bead ring, to avoid accidental aspiration of bead complex. Accordingly, the method further includes manually pipetting at one or more gaps in the wall, wherein the pipet is inserted into the vessel at a gap formed by macromolecule-magnetic bead complexes. The method allows for aspiration of the supernatant with little or no accidental or inadvertent aspiration of the bead complexes, as compared to other magnets that form a continuous ring-shaped band of bead complexes.

In an embodiment, the present invention includes a kit. The kit can comprise a magnet, as described herein, and a vessel for holding liquid samples. Magnetic beads and one or more buffers can also be added as part of the kit in some embodiments.

Additionally disclosed are magnet plate systems for isolating macromolecules. The systems include at least one magnet of the present invention, as well as a top plate, a support plate, and a base plate. One or more springs wound around one or more shoulder posts can also be included as part of the magnet plate systems. The top plate can include a plurality of magnet receivers, and it can accommodate either cylindrical shaped magnets or block shaped magnets.

There are many advantages provided by the present invention. The magnet of the present invention allows for easier pipetting because it allows the use of the vessel wall as a guide for manual insertion of a pipette with more room and at a better angle. The magnet of the present invention provides a magnetic field that allows a bead pattern to form in the vessel that mirrors the segments in the wall which allows for easier aspiration of the solution in the vessel without disturbing the beads. This magnet design allows for easier, more efficient recovery of macromolecules.

BRIEF DESCRIPTION OF THE DRAWINGS

The foregoing and other objects, features, and advantages of the invention will be apparent from the following more particular description of preferred embodiments of the invention, as illustrated in the accompanying drawings in which like parts are referred to by the same reference characters across different views. The drawings are not necessarily to scale, emphasis instead being placed on illustrating the principles of the invention.

FIG. 6A is a schematic of a top view of a magnet plate having multiple discontinuous wall magnets that each has a cylindrical shape.

FIG. 6B is a schematic of a perspective view of a magnet plate shown in FIG. 6A having multiple discontinuous wall magnets that each has a cylindrical shape.

FIG. 6C is a schematic of a side view of a magnet plate shown in FIG. 6A having multiple discontinuous wall magnets that each has a cylindrical shape.

FIG. 6D is a schematic of a front, profile view of a magnet plate shown in FIG. 6A having multiple discontinuous wall magnets that each has a cylindrical shape.

DETAILED DESCRIPTION OF THE INVENTION

Figure 1A:
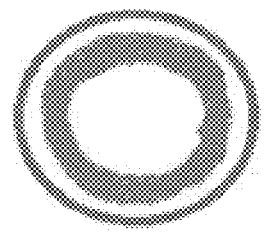
FIG. 1A is a schematic of the formation of macromolecules and paramagnetic beads created by a ring magnet.

A description of preferred embodiments of the invention follows.

In many molecular biology procedures, macromolecules are needed in a purified form. For example, to prepare a DNA or RNA sample for sequencing e.g., Next-Generation-Sequencing (NGS), it can be extracted from any of a variety of clinical sample types, such as tissue, blood, cheek swabs, sputum, forensic material, FFPE samples etc. For example, in certain NGS procedures, the initial extraction from the primary sample is followed by a multitude of enzymatic reactions called library construction. Each enzymatic reaction is followed by another extraction step to isolate conditioned nucleic acid from the reaction mix. The enzymatic reactions are typically followed by amplification (using PCR) and/or size selection (to limit the distribution of fragment sizes to a narrow band of a few hundred basepairs (e.g. 500-700 bp)). The workflow from primary sample to sequencing-ready DNA or RNA may involve from 5-10 separate extraction steps. Throughout the workflow, the overall volume of the mix containing the sample, as well as the sample container can vary significantly; typical volumes range from about 2000 μl to 35 μl. These workflows can be performed manually, or they can be automated to achieve increased throughput and potentially better repeatability.

Depending on the nature of the macromolecule to be extracted as well as the matrix they are present in, magnetic beads (more precisely: paramagnetic beads) are coated with moieties (e.g., functional groups, other compounds) to which the macromolecules have affinity. Macromolecules include nucleic acids (e.g., DNA, RNA, PNA) and proteins (e.g., antibodies, peptides). Essentially, any macromolecule that can be made to adhere, reversibly or not, to magnetic beads can be subjected to the methods disclosed herein. For example, the beads might be coated with a carboxylic acid having moiety such as succinic acid. The coupling between the beads and the macromolecules might also rely on streptavidin-biotin or carbo di-imide chemistry. Exemplary coatings include protein A, protein B, specific antibodies, particular fragments of specific antibodies, streptavidin, nickel, and glutathione. The beads themselves can vary in size, but will have an average diameter (e.g., 1 micro-meter). In some embodiments, the paramagnetic properties of the beads will result from integration of iron into an otherwise non-magnetic substance (e.g., 4% agarose gel). Magnetic beads, as well as those that are already coated with various affinity groups, can be purchased from Sigma-Aldrich Corp. (St. Louis, Mo., USA), Life Technologies (Now part of Thermo Fisher Scientific) (Grand Island, N.Y., USA), Thermo Scientific (Rockford, Ill., USA), EMD-Millipore (Billerica, Mass., USA), New England Biolabs (Ipswich, Mass., USA), GE Healthcare (High Wycombe, UK), and Bangs Laboratories (Indianapolis, Ind.).

In one application of the methods of the present invention, molecules (e.g., macromolecules) can be purified using magnetic beads by performing the following steps:
  a. mixing the magnetic beads having a particular affinity-conferring functional group with the sample matrix containing the molecule of interest in a container (e.g., a vessel, an Eppendorf tube, a microplate well, a deep well, a PCR well, round-bottom vessel);
  b. after the mixing, allowing for specific binding between the beads and the molecules in conditions suitable therefor (e.g., by manipulating the conditions), thus creating bead-molecule complexes;
  c. placing the bottom of the vessel on or inside the hollow core magnet having a discontinuous wall of the present invention;
  d. allowing the bead-molecule complexes to aggregate (e.g., segregate) in a pattern around the inside perimeter of the vessel (or of each vessel if using multiple ones); and
  e. removing the supernatant, which would contain unbound, undesired components;
  f. performing one or more wash steps by adding a suitable solvent, e.g., ethanol, followed by removal of the same.

Additional steps can include re-suspending the bead-molecule complexes in a solvent, so as to obtain a solution with a desired volume and concentration. One can choose the appropriate solvent so that the binding affinity between the beads and the molecules is decreased, allowing them to dissociate from each other. Or one can repeat the steps above to aggregate the magnetic beads again to allow for additional separations, depending on the buffer chosen.

Also the beads may be used to either bind the component of interest, for example nucleic acid molecules, and during the method one discards the supernatant and elutes the component of interest from the beads. Alternatively, one can let the beads bind to a component that one is trying to discard, leaving only the component of interest in the supernatant. In this case, the supernatant is transferred to a new, clean vessel for use or further experimentation and the magnetic beads with their unwanted molecules are discarded.

The above methods can be performed manually or by using automated robotic systems (e.g., automated liquid handling workstations) or aspirating/dispensing manifolds. Usable workstations for automation include Agilent Bravo, the Beckman Biomek i-series, Eppendorf epMotion, Hamilton Star, Tecan Fluent, and many others. When pipetting manually, the technician must take great care to avoid touching the ring of magnetic beads that has formed around the vessel bottom perimeter with the pipet tip, because such contact may cause a portion of the beads, along with their payload (i.e. the extracted macromolecules), to enter the pipet tip and subsequently be aspirated into the tip and discarded along with the supernatant. To avoid touching the beads, the pipet tip needs to be inserted perfectly straight and dead center into the vessel, which requires skill, practice, and dexterity. This task is simplified by the design of the magnet of the present invention having a discontinuous or segmented wall described herein. When magnetic beads are brought into the proximity of the magnet (by placing the vessel on top of the magnet), the beads will aggregate at the location of the highest magnetic field strength, which is generally at the closest distance from the magnet. If the magnet has a segmented wall, the magnetic beads will reflect that pattern and aggregate in a similarly segmented way, leaving one or more gaps in the vessel bottom perimeter. See FIGS. 1B and 1C. This gap provides an opportunity for the technician to slide the pipet tip down along the vessel wall, thus using it as a guide, without disturbing the bead ring, because the pipet tip will slide through the opening in the bead ring that was created by the gap in the segmented magnet wall. This way of pipetting greatly reduces the risk of accidentally disturbing the magnetic beads and the resulting bead loss.

Once a complex is formed between a macromolecule of interest and a magnetic bead (which might be formed via covalent as well as non-covalent bonds), a magnetic field created by a magnet can be employed to separate the bead-macromolecule complexes from the mixture (e.g., by forming one or more bands of beads in the vessel in close proximity to the magnet). After that, the supernatant can be aspirated (e.g., via pipetting) and the complexes washed (e.g., with ethanol) to further remove contaminants. In a subsequent step the macromolecules can be released from the beads, for example by eluting them via changes in the solution (e.g., buffer composition features such as pH and salt concentration). The present invention allows for easier recovery of the eluate since the discontinuous wall allows the user to easily access the eluate without disturbing the bead formation pattern.

The magnet of the present invention, in one embodiment, is made from a rare-earth metal such as neodymium. A neodymium magnet can have the chemical composition $Nd_2Fe_{14}B$, where Nd is neodymium, Fe is iron, and B is boron. In some alternative embodiments, the magnet can also be made from samarium (e.g., sintered $SmCo_5$). The magnet can be covered with a protective layer, for example a layer of nickel. Alternative coatings include one or multiple layers, such as nickel, copper, zinc, tin, silver, gold, epoxy resin, or any other suitable material. Such coatings help, among other things, with preventing rusting of the iron component. In each of these embodiments, the full object is referred to as the "magnet". The magnet can have a strength grade which for different embodiments can be, for example, about N35, N38, N40, N42, N45, N48, N50, or N52. Additional magnets with different grades, such as those with higher N-numbers (those that may be manufactured in the future) or different temperature ranges (H-grades), are also included among the embodiments of the present invention. The magnets (e.g., neodymium magnets) can be sintered or bonded. Magnets can be purchased from K&J Magnetics, Inc., Jamison, Pa. For example, the openings and the discontinuous wall can be molded or machined/drilled after sintering but before coating and magnetization.

In an embodiment, the magnet of the present invention can be used in an electromagnetic arrangement in which the magnet is created by use of a stainless steel or other ferromagnetic structure having a coil or solenoid wrapped around it. The solenoid produces a magnetic field when an electric current is passed through it. This configuration can be used to form the magnet and system of the present invention. This arrangement and others known in the art, or developed in the future, can be used to create the magnet system of the present invention.

Figure 1B:
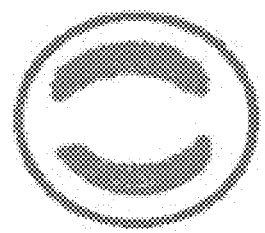
FIG. 1B is a schematic of the formation of macromolecules and paramagnetic beads created by a discontinuous magnet of the present invention having two segments and two gaps in its wall, as shown in FIGS. 2A, 3A, and 4A.
Figure 1C:
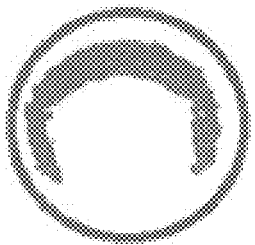
FIG. 1C is a schematic of the formation of macromolecules and paramagnetic beads created by a discontinuous magnet of the present invention having one segment and one gap in its wall, as shown in FIGS. 2B, 3B, and 4B.

The magnet of the present invention has a discontinuous wall instead of a continuous ring shape, such that, when in use, the magnetic field causes the magnetic beads to form a pattern that is discontinuous or has gaps. The discontinuous shape of the wall having one or more gaps corresponds to bead pattern formation having one or more gaps that provide an opening and better angle for insertion of a pipette. FIGS. 1A, 1B and 1C show how and where the paramagnetic beads aggregate, and this occurs because the shape of the magnetic field changed based on the discontinuous ring shape of the magnet. In FIG. 1A, the bead formation was obtained using a ring magnet with a continuous wall. The paramagnetic beads form a ring shape that coincides with the shape of the wall. In FIGS. 1B and 1C, performed with the discontinuous ring magnets shown in FIGS. 2A and 2B, respectively, the paramagnetic beads form a discontinuous or gapped shape (e.g., ring shape) that mirrors the shape of the wall of the discontinuous ring. As can be seen by FIGS. 1B and 1C, the discontinuous wall magnet allows for separation of the magnetic beads but is better suited for manual pipetting. The discontinuous wall allows for a human hand to insert a pipette into the vessel along the side of the vessel and at an angle through an opening/gap in the bead ring that reflects the gap in the wall (FIGS. 1B and 1C), as compared to inserting direct from above (FIG. 1A).

The location of the macromolecule band impacts the steps of the methodology for separating the macromolecules from the mixture. When the vessel is placed on the magnet, the magnetic beads in the solution aggregate near the magnet at the place of the highest concentration of the magnetic field lines; this is where the magnetic field is generally the strongest. The shape or pattern of the bead formation mirrors the shape of the upper portion of the wall and the bead formation generally forms in the bottom of the vessel, near the top of the magnet. The shape of the wall can be chosen based on the separation needs of the user (e.g., manual pipetting, automated pipetting, size of pipettes, volume of mixture, etc.). After discarding the supernatant and washing the immobilized beads with a wash solution, the next step is intended to recover the macromolecules from the beads. This is accomplished by exposing the beads to elution buffer, which will reverse the adherence between the macromolecules and the beads. The purified macromolecules are then present in the elution buffer, which can subsequently be removed from the vessel by aspiration. To effectively elute the macromolecules from the beads, one can add enough elution buffer to completely cover the beads with buffer, so that effective elution can take place. Because it is desirable to keep the elution volume as small as possible (to achieve a higher concentration of eluate) while ensuring complete coverage of the beads by the elution buffer, the magnet of the present invention was designed to aggregate the magnetic beads very low near the bottom of the vessel, regardless of the vessel shape.

Magnetic fields are often visualized using lines. Magnetic field lines are imaginary, but they are helpful tools that illustrate the shape and outline of a magnetic field. In such illustrations the lines emanate from one pole of the magnet and re-enter the magnet at the other pole, thus forming a closed loop. The relative strength of the magnetic field at a given location is shown by varying the density of the lines, with higher densities depicting stronger magnetic fields. The magnetic field is strongest at the magnetic poles. The location of the poles on a particular magnetic shape is determined during manufacturing, when the magnetic material is magnetized. In the present invention, the direction of the magnetization is perpendicular to the surface(s) with the wall, in other words, along the axis of the wall. In particular, the magnets disclosed herein are magnetized through the thickness (i.e., along the center axis running between the top surface plane and the bottom surface plane). Each opening has a top surface and a bottom surface, and each such side (top surface and bottom surface) has a certain polarity, which can be designated as north (N) or south (S). When the magnets having an overall cylindrical shape are assembled on a guide plate (an example of which is shown in FIG. 6A), they can be arranged in any number of arrangements including alternating rows, alternating columns, checkerboard arrangement or other pattern. Arrangements of polarities are embodied for any top plates that might have a different number of magnet receivers to accommodate various size plates (e.g., 6, 24, 96, 384 or even 1536 sample wells arranged in a 2:3 ratio rectangular matrix).

Because the shape of the discontinuous wall magnet of the present invention is different than that of a standard ring-magnet with a continuous wall, the magnetic field lines created are different. In the magnet of the present invention, the magnetic field lines result in stronger pull forces at or near the segments of the wall, thereby providing a gap in the formation of the beads to allow for easier aspiration of the solution.

Specifically, magnets having a discontinuous or segmented wall are useful for manual pipetting to provide a slot or gap into which a pipet can be inserted by a person. The slot allows for a person to access the liquid in the vessel at an angle using the segmented wall as a guide and sliding the pipet tip through the gap or slot in the aggregated paramagnetic beads towards the bottom of the vessel without disturbing the beads.

Figure 2A:
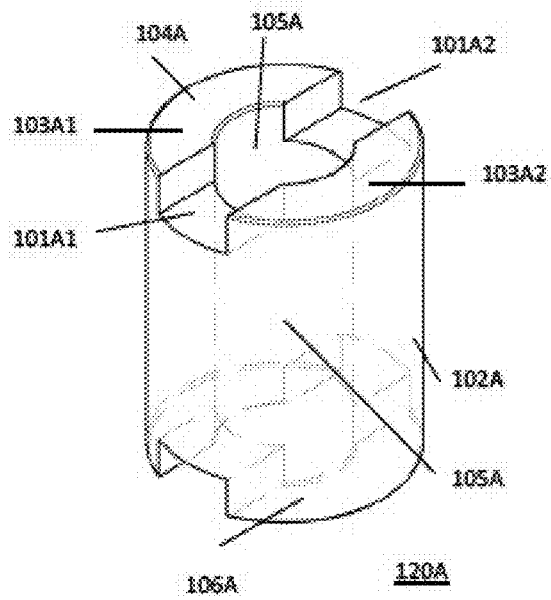
FIG. 2A is a schematic of a perspective view of a hollow core magnet having a discontinuous ring comprising two segments and two gaps.
Figure 2B:
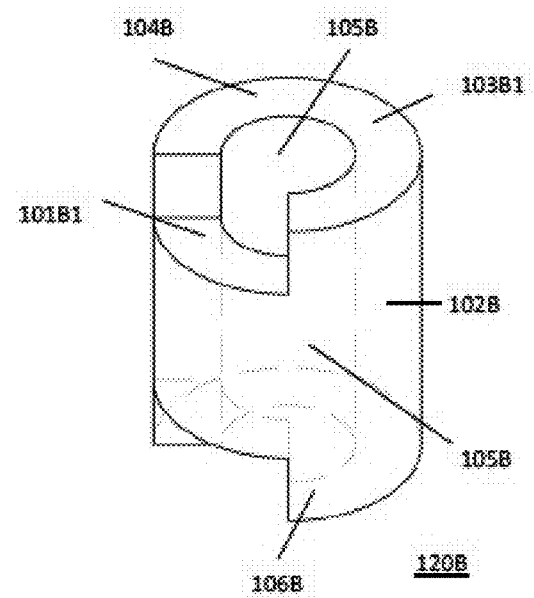
FIG. 2B and FIG. 2C are schematics of a perspective view of a hollow core magnet having a discontinuous ring comprising one segment and one gap.
Figure 2C:
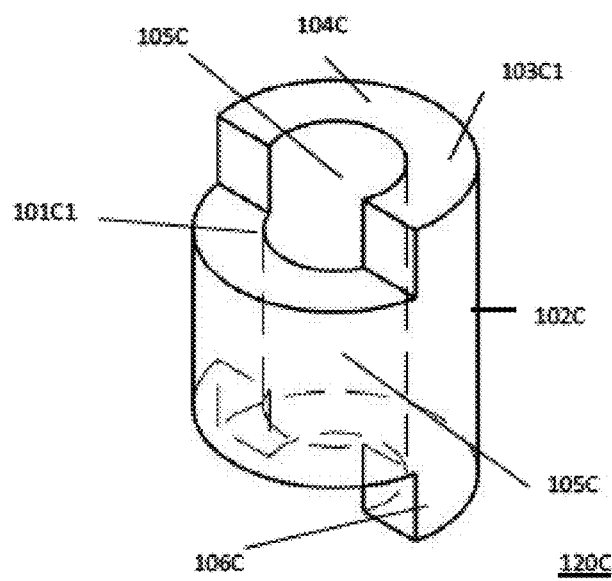

Referring to FIGS. 2A, 2B and 2C show magnets 120A, 120B and 120C. The magnets have a discontinuous wall (e.g., one or more segments (103A1, 103A2, 103B1 and 103C1) and one or more gaps (101A1, 101A2, 101B1 and 101C1)). Accordingly, magnets 120A, 120B and 120C each have a channel or cylindrical opening 105A, 105B and 105C, respectively, that go from top surfaces 104A, 104B, and 104C, and extend to bottom surface 106A, 106B, and 106C, respectively. The sides of magnets 120A, 120B and 120C have side wall 102A, 102B, and 102C, respectively, that form a cylindrical shape but for the gaps (101A1, 101A2, 101B1 and 101C1) in the wall.

The shape and thickness of the opening or channel can be continuous or can vary. In the figures, the cylindrical opening or channel is relatively constant. However, in an embodiment, the channel can be sloped, elliptical, curved or have an irregular shape along its length. For example, a sloped opening that slopes inward to reduce the diameter of the opening as it approaches the center of the magnet can be used to accommodate the shape of vessels that the opening receives. This opening, that travels along the length of the magnet, can be any shape ("V"-like shaped, "U"-like shaped or irregular shape) so long as it can receive the vessel, as described herein.

The overall structure, for magnet 120A, is cylindrical when the presence of a discontinuous wall and the cylindrical opening are ignored. In other words, the volume enclosed inside of the outside wall, bound above by the plane of the top surface (e.g., a first surface) at one end (e.g., top plane), and bound below by the plane of the bottom surface (e.g., a second surface) at another end (e.g., bottom plane) is cylinder-shaped. When referring to volumes, the terms top surface and bottom surface are used to mean the plane of the top surface at one end and the plane of the bottom surface at the other end, respectively.

As described above, the sides of magnets 120A, 120B and 120C are surrounded by side wall 102A, 102B and 102C. In the embodiment shown in FIGS. 2A, 2B, and 2C, both the magnet itself is cylindrical and a portion of the wall is cylindrical-shaped or ring shaped. The openings have walls that are in part cylindrical-shaped and the wall is a discontinuous wall having gaps 101A1 and 101A2 and segments 103A1 and 103A2 such that it forms a discontinuous ring shape. In an embodiment, the wall can be any shape so long as a portion of the wall is discontinuous or segmented (e.g., a discontinuous or segmented ring shape) to form a magnet field that attracts the beads in a discontinuous pattern formation within the vessel. The phrase "discontinuous" or "segmented" is used to refer to at least a portion of the wall that have one or more segments (e.g., one, two, three or four segments) along with one or more gaps, breaks, slots, recesses or the like (e.g., one, two, three or four gaps, respectively).

In an embodiment, the shape of the walls does not need to be a ring shape or cylindrical shape. The wall of the inventive magnet can have at least a top portion that has a discontinuous or segmented shape of a ring, oval, square, rectangular, triangular, diamond, or has a shape that is irregular. The wall has a shape that forms a magnetic field, when in use, within the vessel. The magnetic field, based on the shape of the discontinuous or segmented wall, causes the bead to form in a pattern that mirrors the wall shape to allow for separation. In an embodiment, the discontinuous wall of the inventive magnet can have at least a top portion that has any shape so long as it can receive the vessel and, when in use, the magnetic force emanating from the shape allows the beads/macromolecule complex to aggregate in a pattern such that they can be separated from the mixture.

In FIG. 2A, the wall of discontinuous ring of magnet 120A is formed by two segments and two gaps. FIGS. 2A-2C show several variations of the discontinuous ring. Magnets 120B and 120C shown in FIGS. 2B and 2C have one segment, segment 103B1 or 103C1, respectively, and one gap, gap 101B1 or gap 101E1, respectively. Not shown in the figures, are embodiments having three or four segment/gap series. In each instance, the bead formation mirrors the segments of the discontinuous wall. In the case of a magnet with a four segment/gap series, four partial circular bead formations occur and in the case of magnet 120A two partial circular bead formations occur (see FIG. 1B), whereas in the case of 120B or 120C one partial circular bead formation occurs (see FIG. 1C) which can extend along about half or 180° to about two thirds or 270° (e.g., about 50%, 55%, 60%, 65%, 66%, 70%, 75%, or 80%) of the circumference of the wall.

Figure 3A:
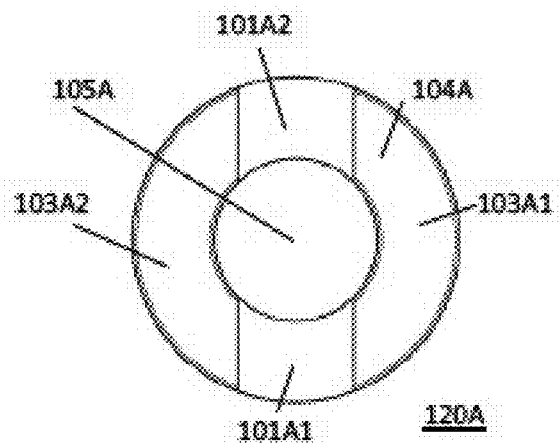
FIG. 3A is a schematic of a top view of a hollow core magnet shown in FIG. 2A having a discontinuous ring comprising two segments and two gaps.
Figure 3B:
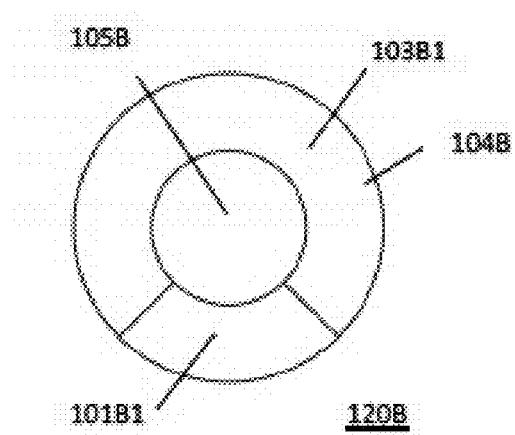
FIG. 3B and FIG. 3C are schematics of a top view of a hollow core magnet shown in FIGS. 2B and 2C having a discontinuous ring comprising one segment and one gap.
Figure 3C:
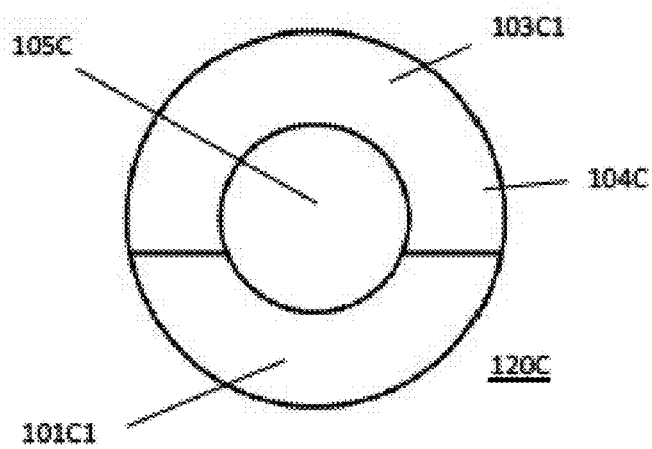

Referring to FIGS. 3A-C, the figure shows the top view of the magnets shown in FIG. 2A-C, respectively. FIGS. 3A, 3B and 3C show the top view of hollow core magnets 120A, 120B and 120C of FIGS. 2A, 2B and 2C, respectively. In these figures, cylindrical openings 105A, 105B and 105C are shown along with the discontinuous ring arrangement of the wall that is made up of segments 103A1 and 103A2 and gaps 101A1 and 101A2, segment 103B1 and gap 101B1, and segment 103C1 and gap 101C1 respectively.

Figure 4A:
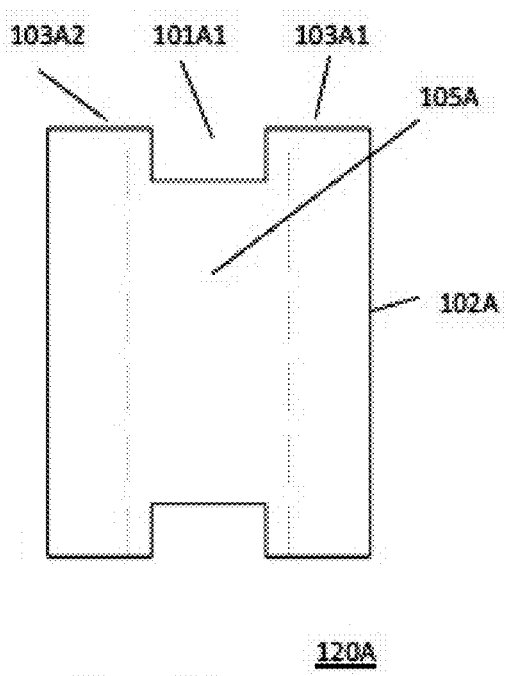
FIG. 4A is a schematic of a side view of a hollow core magnet shown in FIG. 2A having a discontinuous ring comprising two segments and two gaps.
Figure 4B:
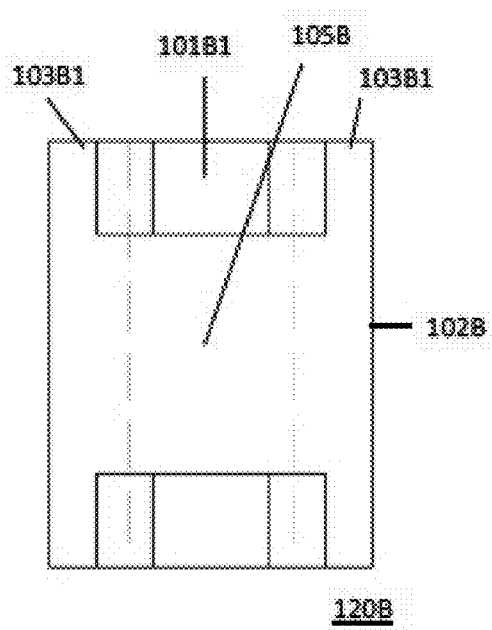
FIG. 4B and FIG. 4C are schematics of a side view of a hollow core magnet shown in FIGS. 2B and 2C having a discontinuous ring comprising one segment and one gap.
Figure 4C:
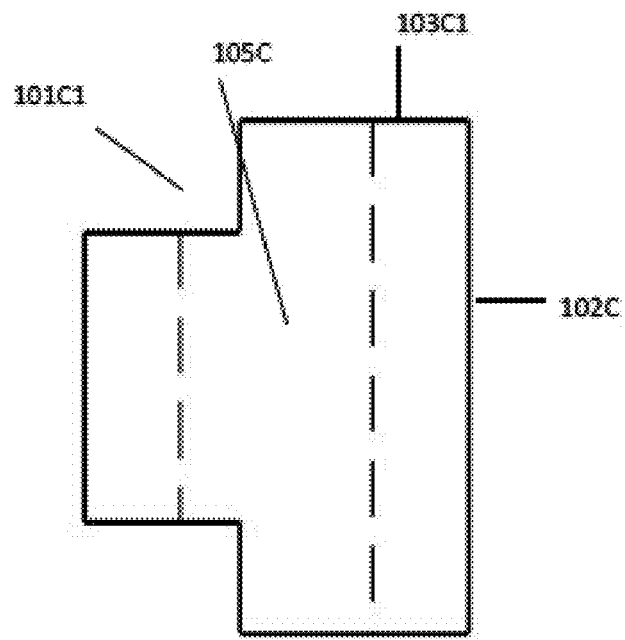

FIGS. 4A-C show a side view of the magnets shown in FIG. 2A-C, respectively. FIGS. 4A, 4B and 4C show the side view of magnets 120A, 120B and 120C, respectively. In these figures, side walls 102A, 102B and 102C and cylindrical openings 105A, 105B and 105C are shown along with the discontinuous ring arrangement made up of two segments 103A1 and 103A2 and two gaps 101A1 and 101A2 (not shown), and a single segment arrangement such as segment 103B1 (FIG. 4B) and segment 103C1 (FIG. 4C) and gap 101B1 (FIG. 4B) and gap 101C1 (FIG. 4C), respectively.

Figure 5:
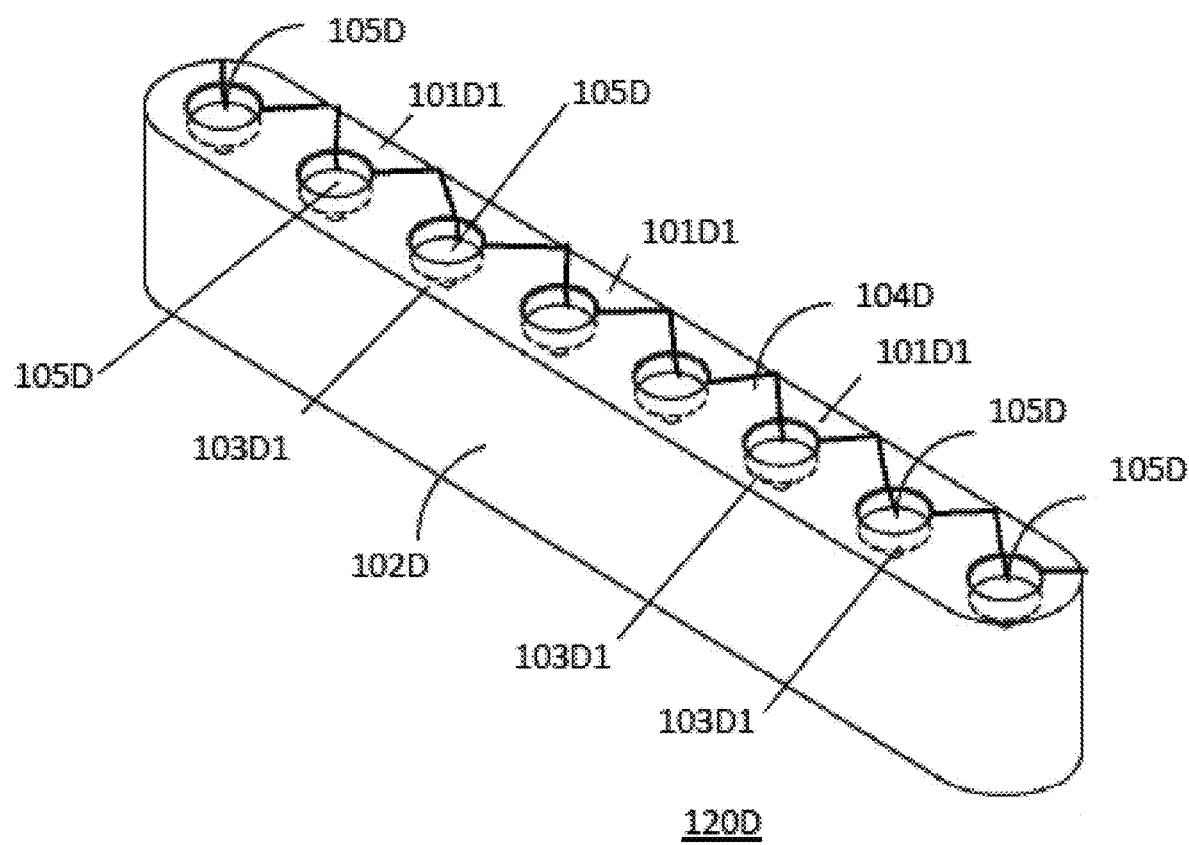
FIG. 5 is a schematic of a perspective view of a block magnet having eight individual discontinuous wall magnets integrated therein.

The magnet of the present invention can be a block magnet having a number of individual openings (e.g., cylindrical opening) integrated therein. In such a case, the discontinuous wall is embedded around each opening, but the overall magnet can be block-shaped, a bar, or a prism (e.g., rectangular-prism shaped), as described herein. Briefly, the overall block shape (or other shape) can have gaps milled, etched, molded, 3D printed, or otherwise inserted to create the discontinuous wall magnet of the present invention. The block magnet can include a plurality of openings (e.g., cylindrical openings) having discontinuous or segmented walls. With respect to the applications of the magnets, the focus is on the discontinuous wall surround the opening, as opposed to the full magnet. For example, both the discontinuous wall magnets and the block magnet having a number of discontinuous walls around openings, are referred to as discontinuous ring magnets, discontinuous wall magnets or discontinuous magnets because regardless of the shape of the overall magnet that has openings/channels with a discontinuous wall. FIG. 5 shows block magnet 120D that is bar magnet having eight cylindrical openings (105D), and eight gaps (101D1) and one segment (103D1) forming individual walls. The segments extend from top surface 104D or bottom surface 106D (not shown), and the entire block magnet 120D is encased by wall 102D. With respect to the applications of the magnets, the focus is on the discontinuous wall, as opposed to the full magnet. Therefore, both the individual magnet (e.g., magnet 120A) and the block magnet (e.g., magnet 120D) are considered and referred to as a discontinuous wall magnet because regardless of the shape of the magnet, it has a discontinuous wall. The phrase "discontinuous wall magnet" in this document refers to magnets that have a discontinuous wall and the wall is being shaped to allow for separation of beads in the vessel.

FIG. 6A shows magnet plate 690, within which there is top plate 92 (also referred to as guide plate) that has 96 magnet receivers (i.e., the holes/openings that receive the magnets not shown in the figure). The magnet receivers are arranged along 8 rows and 12 columns. Each magnet receiver receives a magnet (e.g., 120A, 120B, 120C). Springs are placed around shoulder posts at the corners of the top plate. The shoulder posts, and the springs, pass through top plate 92 and base plate 96. The springs allow flexibility in the leveling of the magnets, and thus any vessels placed in their opening or channel. With the springs, pipetting from the vessels can be accomplished more efficiently. In an embodiment, support plate 94 is a metal, and an affinity exists between the support plate and the magnets. Further underneath, below both the top plate and the support plate, is base plate 96. The top plate can be fastened to the base plate by inserting shoulder posts (e.g., bolts) through the shoulder bolt receivers found at the corners of the two plates. In some embodiments, the shoulder bolts and the springs can be on each of the four corners of the plates, whereas in other embodiments they can be in alternative locations (e.g., along portions of the edges or on some of the corners only). The support plate is made from a material that has affinity to magnets. It can be made from a metal such as iron, nickel, cobalt, or an alloy of different materials (e.g., stainless steel). In a similar fashion to FIG. 6B, FIGS. 6C and 6D show a perspective view, side view and front view of magnet plate 690. The magnet plates can utilize a plurality of single magnets or block magnets.

The integrated spring components enable complete liquid removal without tip occlusion. The springs effectively cushion the wells, and allow the plates (e.g., top plate, support plate) to give way when tips (e.g., pipette tips) come in contact with a well bottom. This compensates for physical tolerances between labware and pipettors, each of which can otherwise compromise the precision of supernatant removal (e.g., aspiration).

In general, the magnets of the present invention, when used for isolating macromolecules, allows easier recovery of the macromolecules, especially when pipetting manually. The magnet of the present invention, as described in the example, provides for better separation of the beads from the mixture. This is accomplished because the design of the magnet provides for a better angle, a guide, and/or space for accessing the solution in the vessel. As compared to a standard ring magnet, the magnet of the present invention has about the same recovery but allows the user to do so in a more accessible fashion. In an embodiment, as compared to a hollow core magnet having a continuous wall (e.g., a standard ring magnet), a percent recovery using the magnet of the present invention having a discontinuous wall is about the same. In another embodiment, the percent recovery increases in a range between about 1% to about 35% (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, or 35%), as compared to the amount recovered using a standard ring/continuous wall magnet.

Standard conditions for forming the macromolecule-bead complex are known in the art and can be found, for example, in Rohland, et al., Cost-Effective High-Throughput DNA Sequencing Libraries For Multiplexed Target Capture, *Genome Research* 22:939-946 and Supplemental Notes (the entire teachings of which are incorporated herein by reference). For example, reagent kits that can be used to form the macromolecule-bead complex are commercially available, such as the AMPURE composition from Beckman Coulter, or such reagents can be made. One example of a solid phase reversible immobilization reagent that can be made and used with the present invention is a MagNA composition, which is made from:

Sera-Mag SpeedBead Carboxylate-Modified Magnetic Particles (Hydrophilic), 100 mL (GE Healthcare Product No. 45152105050350; previously known as 0.1% carboxyl-modified Sera-Mag Magnetic Speed-beads (FisherSci, cat.#: 09-981-123)
18% PEG-8000 (w/v) (e.g. Sigma Aldrich, cat.#: 89510)
1M NaCl
10 mM Tris-HCl, ph 8.0
1 mM EDTA, pH 8.0
Optional: 0.05% Tween 20

To form the macromolecule-bead complex, in one embodiment, 0.5×-3× MagNA in an amount ranging from 10 microliters to 400 microliters can be added to the mixture.

Exemplification

A High Efficiency 96 Well Magnetic Particle Separation Device Designed for Use with Manual Pipettors A. Overview The isolation or purification of macromolecules (e.g., DNA, RNA, and proteins) is routinely required prior to their use in a multitude of applications. The use of magnetic particles coated with a variety of functional groups is widely used for these applications. Although initially most commonly used in high throughput workflows in conjunction with liquid handling robotics, magnetic particles are increasingly used in low to moderate throughput workflows due to their ease of use, efficiency, and low cost. In a typical low to moderate throughput workflow users accomplish liquid transfer steps using multi or single channel manual pipettors in conjunction with a 96 well magnetic particle separator. Efficient separation and recovery of the paramagnetic particles complexed to the desired macromolecule is dependent on a number of factors; viscosity and volume of the liquids being used, the type and design of the vessel or labware being employed, and importantly the design of the magnetic particle separator. For manual users the magnetic plate must employ powerful magnets and collect the magnetic particles in a fashion that minimizes any inadvertent bead loss due to variations of individual pipetting techniques.

To this end, a novel highly powerful magnetic particle separator, a gapped or a slotted ring magnet ("SRM"), was designed and tested. The SRM used in the experiment had two segments and two gaps, as shown in FIGS. 2A, 3A, 4A, and 6. This magnet collects and concentrates the magnetic particles into opposing regions near the bottom of the labware wells, as shown in FIG. 1B. The gapped/slotted design allows manual users greater flexibility in their approach to removing supernatants with a higher degree of confidence that magnetic particles will not be inadvertently aspirated during any sample processing steps.

The data below for a discontinuous wall magnet or SRM demonstrates the advantage of its design when using paramagnetic particles complexed to nucleic acid molecules and extracted by using manual pipettors and a commonly used magnetic particle purification chemistry.

B. Methods and Materials

1) Assembly of magnetic particle purification chemistry (MPPC).

50 mLs of a solution containing the following components was assembled:
10 gms of 20% PEG-8000 (w/v), Sigma, cat.#: 89510
20 mL of 5M NaCl, Sigma, cat.#: S7653
500 uL of 100× Tris-EDTA Buffer Solution, Sigma T9285-100
Add Sigma Nuclease Free Water PN:W4502, to a final volume of 50 mL.
Mix all components until solution is clear.
Add 1.2 mLs of Sera-Mag Magnetic Carboxylate Modified Particles.
Mix solution again until magnetic particles are evenly dispersed.

2) Recovery Testing in 96-well Costar round bottom microplates, (Corning, Inc., Cat.#: 3795)

(a) A master mixture of 112 uL of lambda DNA (New England BioLabs, PN: N3011S) at 500 ng/uL, 56 uL Bovine Serum Albumin (BSA Solution, Ambion, PN: AM2616) at 50 mg/mL, 2.8 mL of 1× Tris-EDTA diluted in nuclease free water (100× Tris-EDTA Buffer Solution (Sigma T9285-100 —diluted in Sigma Nuclease Free Water PN:W4502, and 5 mL of WPC (see section 1 above) was assembled and gently mixed.

The mixture was allowed to incubate for 5 minutes at room temperature. 300 uL of the master mixture was added to row A of two separate round bottom microplates using a 1000 uL single channel pipettor (Rainin, Cat.#: 17014382).

One round bottom microplate was placed on the SRM plate with the other plate being placed on a regular ring magnet plate. Both microplates were incubated for 7 minutes to allow the magnetic particles to be collected. To mimic inadvertent particle aspiration, wells A1 through A6 were aspirated using a tracking aspiration (removal of liquid as the pipet tip is moving downward) with contact to the left side of the wells as the pipet tip was lowered to the bottom of the well, referred to as the TSW (Tracking Side of Well) method. In wells A7 through A12 the liquid was aspirated using a tracking aspiration with no contact to the sides of the wells, referred to as the TDC (Tracking Dead-Center) method. These aspiration procedures were used for all steps in the purification process including ethanol washes and elution. Following supernatant removal the plates were washed two times with 300 uL 75% ethanol (from a master mix of 75 mL of Ethanol (98%)(Sigma, cat.#E7023) and 25 mL of nuclease free water (Sigma, cat.#W4502).

Washing is performed in the following manner: Remove microplate from the magnetic separator; add ethanol, resuspend beads, incubate for 30 seconds, place microplate on magnetic separator, and wait for the beads to collect before removing supernatant.

Following the final ethanol wash, the particles were allowed to dry with the microplates on the magnetic plates for 7 minutes. Lambda DNA was eluted in 50 uL of 1× Tris-EDTA (as prepared above). DNA concentration in the eluted samples was measured using a DeNovix Model DS-11 Series spectrophotometer. Data was recorded in Table 1 below.

C. Data and Analysis

TABLE 1

Recovery of lambda DNA from round bottom plates - SRM and regular ring magnet plate.

| | SRM | | Regular Ring Magnet Plate | | |
|---|---|---|---|---|---|
| Aspiration Method | Well Location | Lambda DNA Conc. (ng/uL) | Aspiration Method | Well Location | Lambda DNA Conc. (ng/uL) |
| TSW* | A1 | 35.2 | TSW* | A1 | 26.2 |
| TSW* | A2 | 35.6 | TSW* | A2 | 28.1 |
| TSW* | A3 | 34.7 | TSW* | A3 | 24.2 |
| TSW* | A4 | 34.8 | TSW* | A4 | 22.5 |
| TSW* | A5 | 35.1 | TSW* | A5 | 26.5 |
| TSW* | A6 | 34.9 | TSW* | A6 | 24.0 |
| TDC** | A7 | 34.8 | TDC** | A7 | 35.0 |
| TDC** | A8 | 36.1 | TDC** | A8 | 34.6 |
| TDC** | A9 | 35.4 | TDC** | A9 | 34.8 |
| TDC** | A10 | 35.7 | TDC** | A10 | 35.9 |
| TDC** | A11 | 36.0 | TDC** | A11 | 36.2 |
| TDC** | A12 | 33.9 | TDC** | A12 | 36.0 |

*TSW = Aspirate while tracking down side of well
**TDC = Aspirate while tracking dead-center to bottom of well without contact with side of well 1. Analysis

| | |
|---|---|
| Mean of SRM-TSW Method: | 35.1 ng/ul |
| Mean of SRM-TDC Method: | 35.3 ng/ul |
| Mean of Regular Ring Magnet Plate - TSW Method: | 25.3 ng/ul |
| Mean of Regular Ring Magnet Plate - TDC Method: | 35.4 ng/ul |
| % Difference mean of SRM-TSW method vs mean of regular ring TSW method: | 28.0 |
| % Difference mean of SRM-TDC method vs mean of regular ring TDC method: | 0.99 |
| STD Dev of SRM-TSW Method: | 0.3 ng/ul |
| STD Dev of SRM-TDC Method: | 0.8 ng/ul |
| STD Dev of Regular Ring Mag. - TSW Method: | 2.2 ng/ul |
| STD Dev of Regular Ring Mag. - TDC Method: | 0.7 ng/ul |

D. Conclusion

Based on the analysis of the data use of the slotted/discontinuous wall magnetic plate or SRM resulted in a 28% increase in lambda DNA recovery when using the TSW tracking aspiration method, namely using the gap in the wall along the side of the wall, as compared to the regular ring magnet plate having a continuous wall with no gaps for the Costar round bottom plate.

In addition, no significant difference in lambda DNA recovery was observed between the slotted/discontinuous wall magnet plate and the continuous wall magnet plate using the TDC method to aspirate-while-tracking to bottom of well without contact with the sides of well, indicating no reduction in performance when using the slotted plate design.

In conclusion, the slotted/discontinuous wall magnet plate design significantly mitigates inadvertent loss of magnetic particles due to variations in pipetting techniques for manual users of magnetic particle-based workflows.

The relevant teachings of all the references, patents and/or patent applications cited herein are incorporated herein by reference in their entirety.

The following applications are related to the invention described herein: U.S. Application No. (not yet assigned), entitled "Solid-Core Magnet" by Olaf Stelling, filed (on even date herewith); U.S. application Ser. No. 15/497,858, entitled "Solid-Core Ring-Magnet" by Olaf Stelling, filed Apr. 26, 2017; U.S. application Ser. No. 14/515,256, entitled "SOLID-CORE RING-MAGNET" by Olaf Stelling, filed Oct. 15, 2014. The entire teachings of the above application are incorporated herein by reference.

While this invention has been particularly shown and described with references to preferred embodiments thereof, it will be understood by those skilled in the art that various changes in form and details may be made therein without departing from the scope of the invention encompassed by the appended claims.

What is claimed is:

1. A magnet for use in isolating macromolecules from a mixture in a vessel when the macromolecules adhere to paramagnetic beads to form a complex, wherein the magnet comprises:
   a. a cylindrical wall defining a cylindrical opening extending from a first end having a first surface to a second end having a second surface; and
   b. one or more discontinuous walls wherein at least a portion of the discontinuous wall comprises one or more segments and one or more gaps, wherein at least a portion of the discontinuous wall extends from the cylindrical wall;
   wherein the discontinuous wall forms a shape configured to form a magnetic field, when in use, within the vessel.

2. The magnet of claim 1, wherein the discontinuous wall forms a discontinuous pattern in the vessel such that, when in use, the complex of macromolecules and paramagnetic beads aggregate and can be separated from the mixture.

3. The magnet of claim 1, wherein the discontinuous wall has one, two, three or four segments separated by one, two, three or four gaps, respectively, to form a discontinuous shape.

4. The magnet of claim 1, wherein at least the portion of the discontinuous wall is shaped to form a discontinuous ring, oval, square, rectangular, triangular, diamond, or an irregular shape.

5. The magnet of claim 1, wherein the magnet is made from one or more pieces.

6. A magnet for use in isolating macromolecules from a mixture in a vessel when the macromolecules adhere to paramagnetic beads to form a complex, wherein the magnet comprises:
   a. a wall defining a lengthwise opening extending from a first end having a first surface to a second end having a second surface; and
   b. one or more discontinuous walls wherein at least a portion of the discontinuous wall comprises one or more segments and one or more gaps, wherein at least a portion of the discontinuous wall extends from the wall;
   wherein the discontinuous wall forms a shape configured to form a magnetic field, when in use, within the vessel.

7. The magnet of claim 6, wherein the discontinuous wall forms a discontinuous pattern in the vessel such that, when in use, the complex of macromolecules and paramagnetic beads aggregate and can be separated from the mixture.

8. The magnet of claim 6, wherein the discontinuous wall has one, two, three or four segments separated by one, two, three or four gaps, respectively, to form a discontinuous shape.

9. The magnet of claim 6, wherein at least the portion of the discontinuous wall is shaped to form a discontinuous ring, oval, square, rectangular, triangular, diamond, or an irregular shape.

10. The magnet of claim 6, wherein the magnet is made from one or more pieces.

11. A method for purifying a macromolecule from a liquid sample having a mixture, the method comprising:
   a. collecting the liquid sample in a vessel;
   b. adding magnetic beads to the liquid sample, wherein steps "a" and "b" can be performed in any order under conditions to form a macromolecule-magnetic bead complex between the macromolecule and the magnetic bead;
   c. separating the complex from the sample by placing the vessel on the magnet or at the magnet, wherein the magnet comprises:
      i. a wall defining a lengthwise opening extending from a first end having a first surface to a second end having a second surface; and
      ii. one or more discontinuous walls wherein at least a portion of the discontinuous wall comprises one or more segments and one or more gaps, wherein at least a portion of the discontinuous wall extends from the wall;
   wherein the discontinuous wall forms a shape configured to form a magnetic field, when in use, within the vessel.

12. The method of claim 11, wherein the magnet is made from one or more pieces.

13. The method of claim 11, comprising the step of pipetting sample manually or using an automated pipette.

14. The method of claim 13, wherein the step of manually pipetting occurs at one or more gaps in the cavity wall, wherein the pipette is inserted into the vessel at a gap formed by macromolecule-magnetic bead complexes.

15. The method of claim 11, further comprising the step of eluting the macromolecule from the magnetic beads.

16. The method of claim 11, wherein the sample comprises an extracellular matrix, cell debris, plasma, saliva, or a combination thereof.

17. The method of claim 11, further comprising a step of lysing the sample before adding magnetic beads to the sample.

18. A kit for use in isolating macromolecules from a mixture in a vessel when the macromolecules adhere to paramagnetic beads to form a complex, wherein the kit comprises:
   a. a magnet that comprises:
      i. a wall defining a lengthwise opening extending from a first end having a first surface to a second end having a second surface; and
      ii. one or more discontinuous walls wherein at least a portion of the discontinuous wall comprises one or more segments and one or more gaps, wherein at least a portion of the discontinuous wall extends from the wall;
   wherein the discontinuous wall forms a shape configured to form a magnetic field, when in use, within the vessel; and
   b. the vessel for holding the mixture having the macromolecule, wherein the vessel is placed on the magnet or is shaped to fit within the one or more openings.

19. The kit of claim 18, wherein the magnet is made from one or more pieces.

20. The kit of claim 18, wherein the discontinuous wall forms a shape configured such that, when in use, the complex of macromolecules and paramagnetic beads aggregate in a pattern such that they can be separated from the mixture.

21. The kit of claim 18, wherein at least the portion of the discontinuous wall is shaped to form a discontinuous ring, oval, square, rectangular, triangular, diamond, or an irregular shape.

22. The kit of claim 18, wherein the kit further comprises magnetic beads.

23. The kit of claim 18, wherein the kit further comprises one or more buffer compositions.

24. A magnet plate system for use in isolating a macromolecule from a mixture in a vessel, wherein the magnet plate comprises:
   a. at least one magnet, wherein the magnet comprises:
      i. a wall defining a lengthwise opening extending from a first end having a first surface to a second end having a second surface; and
      ii. one or more discontinuous walls wherein at least a portion of the discontinuous wall comprises one or more segments and one or more gaps, wherein at least a portion of the discontinuous wall extends from the wall;
   wherein the discontinuous wall forms a shape configured to form a magnetic field, when in use, within the vessel; and
   b. a top plate adapted to receive a plurality of magnets, wherein the top plate has one or more post openings for receiving a top end of a post and a spring;
   c. a post having a top end and a bottom end;
   d. a spring for placement at the opening of the top plate and surrounding the post;
   e. a support plate to support the magnet, wherein an affinity exists between the support plate and the magnet; and
   f. a base plate receives the bottom end of the post and the spring and is placed underneath the base plate when in use.

25. The magnet plate system of claim 24, wherein the magnet is made from one or more pieces.

26. The magnet plate system of claim 24, wherein the top plate comprises a plurality of magnet openings to receive the magnets.

* * * * *